United States Patent
Shimizu et al.

(10) Patent No.: US 10,253,128 B2
(45) Date of Patent: Apr. 9, 2019

(54) CROSSLINKING AGENT AND FLUORINE-CONTAINING AROMATIC COMPOUND

(71) Applicant: NICHIAS CORPORATION, Tokyo (JP)

(72) Inventors: Tomoya Shimizu, Tokyo (JP); Ayumi Maezawa, Tokyo (JP); Yuriko Sekimoto, Tokyo (JP); Naoya Kuzawa, Tokyo (JP)

(73) Assignee: NICHIAS CORPORATION, Tokyo (JP)

( * ) Notice: Subject to any disclaimer, the term of this patent is extended or adjusted under 35 U.S.C. 154(b) by 0 days.

(21) Appl. No.: 14/910,828

(22) PCT Filed: Jul. 30, 2014

(86) PCT No.: PCT/JP2014/004007
§ 371 (c)(1),
(2) Date: Feb. 8, 2016

(87) PCT Pub. No.: WO2015/019581
PCT Pub. Date: Feb. 12, 2015

(65) Prior Publication Data
US 2016/0185892 A1 Jun. 30, 2016

(30) Foreign Application Priority Data
Aug. 7, 2013 (JP) .................................. 2013-164589

(51) Int. Cl.
| C08K 5/03 | (2006.01) |
| C08F 259/08 | (2006.01) |
| C07C 22/08 | (2006.01) |
| C09K 3/10 | (2006.01) |
| F16J 15/10 | (2006.01) |
| C07C 43/29 | (2006.01) |

(52) U.S. Cl.
CPC ............ C08F 259/08 (2013.01); C07C 22/08 (2013.01); C07C 43/29 (2013.01); C08K 5/03 (2013.01); C09K 3/1009 (2013.01); F16J 15/102 (2013.01)

(58) Field of Classification Search
CPC ........... C08K 5/03; C07C 22/08; C07C 43/29; C09K 3/1009
See application file for complete search history.

(56) References Cited

U.S. PATENT DOCUMENTS

| 5,023,380 A | 6/1991 | Babb et al. |
| 5,037,917 A * | 8/1991 | Babb ............... C07C 17/269 526/242 |
| 5,037,918 A | 8/1991 | Babb |
| 5,066,746 A | 11/1991 | Clement et al. |
| 5,159,036 A | 10/1992 | Babb |
| 5,159,037 A | 10/1992 | Clement et al. |
| 5,159,038 A | 10/1992 | Babb et al. |
| 5,162,468 A | 11/1992 | Babb et al. |
| 5,246,782 A | 9/1993 | Kennedy et al. |
| 5,364,547 A | 11/1994 | Babb et al. |
| 5,364,917 A | 11/1994 | Babb et al. |
| 5,409,777 A | 4/1995 | Kennedy et al. |
| 5,730,922 A | 3/1998 | Babb et al. |
| 6,703,461 B1 | 3/2004 | Tanaka et al. |
| 2003/0049399 A1 | 3/2003 | Noguchi et al. |
| 2004/0147698 A1 | 7/2004 | Tanaka et al. |
| 2005/0014917 A1 | 1/2005 | Michot et al. |
| 2005/0282969 A1 | 12/2005 | Comino et al. |
| 2007/0135577 A1 * | 6/2007 | Shefelbine ............... C08L 27/20 525/199 |

FOREIGN PATENT DOCUMENTS

| CN | 1787900 A | 6/2006 |
| CN | 1944521 A | 4/2007 |
| JP | 57-200476 A | 12/1982 |
| JP | 4-500367 A | 1/1992 |
| JP | 4-500388 A | 1/1992 |
| JP | 11-199743 A | 7/1999 |
| JP | 2000-327846 A | 11/2000 |
| JP | 2003-208983 A | 7/2003 |
| JP | 2006-009010 A | 1/2006 |
| JP | 2007-154043 A | 6/2007 |
| JP | 2009-242782 A | 10/2009 |
| JP | 2012-211347 A | 11/2012 |

(Continued)

OTHER PUBLICATIONS

Saito et al. Journal of Organic Chemistry, 66, 796-802 (Year: 2001).*

(Continued)

Primary Examiner — Mark S Kaucher
(74) Attorney, Agent, or Firm — Griffin and Szipl PC

(57) ABSTRACT

A crosslinking agent includes a compound represented by the following formula (1). In the formula (1), $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, m is an integer of from 2 to 6, l is an integer of from 0 to 2, and each hydrogen on the benzene ring(s) is optionally substituted with a substituent.

(1)

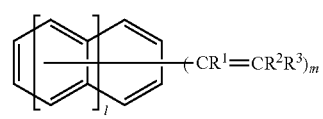

20 Claims, No Drawings

(56) References Cited

FOREIGN PATENT DOCUMENTS

| WO | 98/36901 A1 | 8/1998 |
|----|-------------|--------|
| WO | 2004/103677 A1 | 12/2004 |
| WO | 2012/069133 A1 | 5/2012 |

OTHER PUBLICATIONS

Morken et al. Journal of Organic Chemistry, 58, 1167-1172 (Year: 1993).*
Brisdon et al. Organometallics 31, 1341-1348 (Year: 2012).*
Reynolds et al. Journal of Organic Chemistry 55, 14, 4448-4454 (Year: 1990).*
A. Raghavanpillai, et al., J. Org. Chem., 2004, vol. 69, pp. 7083-7091.
International Search Report issued in corresponding application PCT/JP2014/004007, completed Oct. 23, 2014 and mailed Nov. 4, 2014.
International Preliminary Report on Patentability issued in corresponding application PCT/JP2014/004007 issued in Feb. 9, 2016.
Extended European Search Report issued in corresponding application 14834698.4, completed May 3, 2017 and dated May 17, 2017.
Office Action issued in Chinese patent application 201480044666.5 dated Mar. 30, 2017 (no translation available; submitted for certification).
Office Action issued in corresponding Chinese application 201480044666.5, dated May 15, 2018.

* cited by examiner

CROSSLINKING AGENT AND FLUORINE-CONTAINING AROMATIC COMPOUND

This is a National Phase Application in the United States of International Patent Application No. PCT/JP2014/004007 filed Jul. 30, 2014, which claims priority on Japanese Patent Application No. 2013-164589, filed Aug. 7, 2013. The entire disclosures of the above patent applications are hereby incorporated by reference.

TECHNICAL FIELD

The invention relates to a crosslinking agent, a composition that includes a crosslinking agent, a crosslinked fluoroelastomer, a formed article that is obtained by using a crosslinked fluoroelastomer, and a fluorine-containing aromatic compound.

BACKGROUND ART

Water vapor is used in various industries (e.g., plant industry, machine industry, food industry, and medical industry) for power generation, sterilization, cleaning (washing), and the like. A seal material (e.g., rubber O-ring) is used for a pipe and a device in which water vapor flows, and prevents water vapor from flowing to the outside.

In recent years, there has been a tendency that the temperature of water vapor used in a power plant is increased in order to improve the power generation efficiency. Therefore, high-temperature water vapor resistance has been desired for a seal material. In such a case, a seal material formed of a crosslinked fluoroelastomer (e.g., fluororubber or perfluororubber) is used. However, since a seal material formed of a crosslinked fluoroelastomer may have poor vapor resistance, a further improvement has been desired (see Patent Literature 1, for example).

A crosslinking agent is used when producing a crosslinked fluoroelastomer, and various crosslinking agents have been known. For example, triallyl isocyanurate (TAIC) is widely used as such a crosslinking agent (see Patent Literature 2 to 6, for example), and divinylbenzene (see Patent Literature 2 to 5, for example), divinylbiphenyl (see Patent Literature 5, for example), and the like are also used.

However, a novel crosslinking agent that can further improve the heat resistance and the vapor resistance of a crosslinked fluoroelastomer has been desired.

Patent Literature 6 discloses tetrafluoroethylene and a perfluoroalkyl vinyl ether as a raw material monomer for producing a fluoroelastomer.

Non-Patent Literature 1 discloses 1,2,2-trifluorostyrene (perfluorovinylbenzene) as a material for producing a fuel cell separation membrane.

CITATION LIST

Patent Literature

Patent Literature 1: JP-A-2006-9010
Patent Literature 2: JP-A-2009-242782
Patent Literature 3: JP-A-H11-199743
Patent Literature 4: WO1998/036901
Patent Literature 5: JP-A-2000-327846
Patent Literature 6: JP-A-2012-211347

Non-Patent Literature

Non-Patent Literature 1: A. Raghavanpillai, et al., J. Org. Chem., 2004, vol. 69, pp. 7083-7091

SUMMARY OF INVENTION

The invention was conceived in view of the above problem. An object of the invention is to provide a crosslinking agent that can improve the heat resistance and the vapor resistance of a crosslinked fluoroelastomer, and a crosslinked fluoroelastomer that exhibits improved heat resistance and vapor resistance.

Another object of the invention is to provide a novel fluorine-containing aromatic compound that can be used as a crosslinking agent.

According to one aspect of the invention, a crosslinking agent includes a compound represented by the following formula (1),

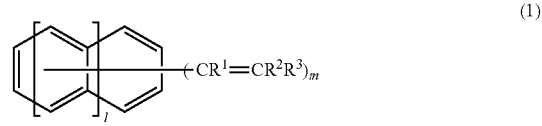

wherein $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, m is an integer of from 2 to 6, l is an integer of from 0 to 2, and each hydrogen on the benzene ring(s) is optionally substituted with a substituent.

According to another aspect of the invention, a crosslinking agent includes a compound that includes two or more structures represented by the following formula (3),

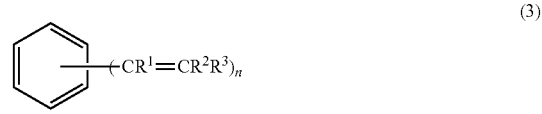

wherein $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, n are independently an integer of from 1 to 5, and each hydrogen on the benzene rings is optionally substituted with a substituent.

According to another aspect of the invention, a composition includes a fluoroelastomer, an initiator, and the crosslinking agent.

According to another aspect of the invention, a crosslinked fluoroelastomer is obtained by crosslinking the composition.

According to another aspect of the invention, a formed article is formed of the crosslinked fluoroelastomer.

According to another aspect of the invention, a compound is represented by the following formula (1),

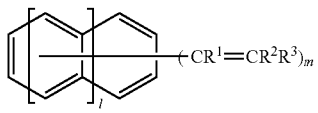

(1)

wherein $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, m is an integer of from 2 to 6, l is an integer of from 0 to 2, and each hydrogen on the benzene ring(s) is optionally substituted with a substituent.

According to another aspect of the invention, a compound is represented by the following formula (4),

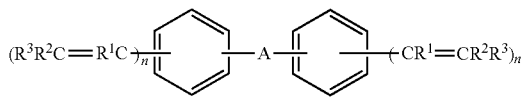

(4)

wherein A is a single bond, —O—, —S—, a heteroatom-containing group, a linear or a branched alkylene group, a cycloalkylene group, or an arylene group that is optionally fluorinated either partially or completely, $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, n are independently an integer of from 1 to 5, and a compound in which A is a single bond, $R^1$, $R^2$, and $R^3$ are a fluorine atom, and n are 1 is excluded, and each hydrogen on the benzene rings is optionally substituted with a substituent.

According to another aspect of the invention, a compound is represented by the following formula (5),

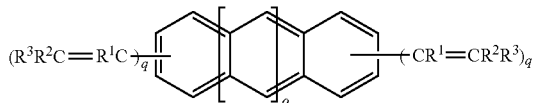

(5)

wherein $R^1$, $R^2$, and $R^3$ are independently a fluorine atom, an alkyl group, a fluoroalkyl group, or a substituted or unsubstituted aryl group, a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, o is 1 or 0, q are independently an integer of from 1 to 3, and each hydrogen on the benzene rings is optionally substituted with a substituent.

According to a further aspect of the invention, a crosslinked fluoroelastomer has a change ratio of 70% or less with respect to a weight swelling ratio when exposed to saturated water vapor at 300° C. for 22 hours, the weight swelling ratio being measured after immersing the crosslinked fluoroelastomer in a perfluorocarbon solution at 21 to 25° C. for 72 hours.

Advantageous Effects of Invention

The invention thus provides a crosslinking agent that can improve the heat resistance and the vapor resistance of a crosslinked fluoroelastomer, and a crosslinked fluoroelastomer that exhibits improved heat resistance and vapor resistance.

The invention thus also provides a novel fluorine-containing aromatic compound that can be used as a crosslinking agent.

DESCRIPTION OF EMBODIMENTS

Exemplary embodiments of the invention are described below. Note that the invention is not limited to the following exemplary embodiments.

A crosslinking agent according to one embodiment of the invention includes a compound represented by the following formula (1).

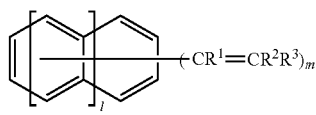

(1)

$R^1$, $R^2$, and $R^3$ in the formula (1) are independently a fluorine atom, an alkyl group, a fluoroalkyl group, or a substituted or unsubstituted aryl group. A plurality of $R^1$ are identical or different. A plurality of $R^2$ are identical or different. A plurality of $R^3$ are identical or different. Note that at least one of $R^1$, $R^2$, and $R^3$ is a fluorine atom or a fluorine atom-containing group. Examples of the fluorine atom-containing group include a fluoroalkyl group, and an aryl group that is substituted with a fluorine atom or a fluoroalkyl group.

The alkyl group and the alkyl group included in the fluoroalkyl group may be linear or branched. The number of carbon atoms of the alkyl group is preferably 1 to 15 (more preferably 1 to 6).

The fluoroalkyl group has a structure in which the alkyl group is fluorinated partially or completely. The fluoroalkyl group is preferably a perfluoroalkyl group.

The number of carbon atoms of the aryl group is preferably 6 to 18 (more preferably 6 to 12). Examples of the aryl group include a phenyl group, a naphthyl group, and the like.

Examples of a substituent that may substitute the aryl group include a fluorine atom, a linear or branched alkyl group, a cycloalkyl group, an aryl group, and the like. These groups may be fluorinated partially or completely. The number of carbon atoms of the linear or branched alkyl group is preferably 1 to 15 (more preferably 1 to 6). The number of carbon atoms of the cycloalkyl group is preferably 3 to 8 (more preferably 3 to 6). The number of carbon atoms of the aryl group is preferably 6 to 18 (more preferably 6 to 12).

It is preferable that $R^1$, $R^2$, and $R^3$ be independently a fluorine atom, an alkyl group, or a fluoroalkyl group. It is preferable that two or more of $R^1$, $R^2$, and $R^3$ be a fluorine atom. It is more preferable that all of $R^1$, $R^2$, and $R^3$ be a fluorine atom.

Examples of the group represented by —CR$^1$=CR$^2$R$^3$ (fluorine-containing substituted vinyl group) include the following groups. Note that m groups represented by —CR$^1$=CR$^2$R$^3$ are identical or different.

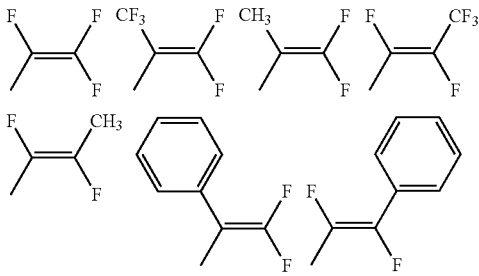

m in the formula (1) is 2, 3, 4, 5, or 6, and preferably 2.

l in the formula (1) is 0, 1, or 2. l is preferably 0.

Examples of the compound represented by the formula (1) include the compounds respectively represented by the following formulas (2), (6), and (7).

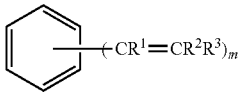

(2)

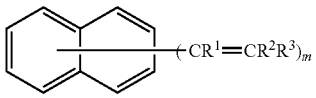

(6)

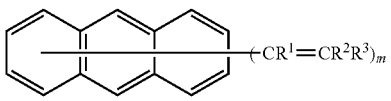

(7)

R$^1$, R$^2$, R$^3$, and m in the formulas (2), (6), and (7) are the same as defined above.

When m in the formula (2) is 2, two groups represented by —CR$^1$=CR$^2$R$^3$ may be situated at ortho positions, meta positions, or para positions. It is preferable that two groups represented by —CR$^1$=CR$^2$R$^3$ be situated at para positions.

A crosslinking agent according to another embodiment of the invention includes a compound that includes two or more structures represented by the following formula (3). The benzene ring included in the formula (3) may be bonded to another group or ring, and may be fused with another ring.

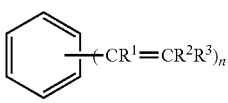

(3)

R$^1$, R$^2$, and R$^3$ in the formula (3) are the same as defined for the formula (1). n are independently 1, 2, 3, 4, or 5.

Examples of a preferable compound that includes two or more structures represented by the formula (3) include a compound represented by the following formula (4).

(4)

A in the formula (4) is a single bond, —O—, —S—, a heteroatom-containing group, a linear or a branched alkylene group, a cycloalkylene group, or an arylene group that is optionally fluorinated partially or completely. For example, the alkylene group, the cycloalkylene group, and the arylene group are optionally fluorinated.

The number of carbon atoms of the linear or branched alkylene group is preferably 1 to 15 (more preferably 1 to 6). The number of carbon atoms of the cycloalkylene group is preferably 3 to 8 (more preferably 3 to 6). The number of carbon atoms of the arylene group is preferably 6 to 18 (more preferably 6 to 12).

Examples of the alkylene group include a methylene group, an ethylene group, a propylene group, and the like. Examples of the arylene group include a phenylene group, a naphthalenylene group, and the like.

R$^1$, R$^2$, R$^3$, and n in the formula (4) are the same as defined above.

When n in the formula (4) are 1, A and the group represented by —CR$^1$=CR$^2$R$^3$ may be situated at ortho positions, meta positions, or para positions. It is preferable that A and the group represented by —CR$^1$=CR$^2$R$^3$ be situated at para positions. It is more preferable that A and each of the groups represented by —CR$^1$=CR$^2$R$^3$ be situated at para positions.

Specific examples of the compound represented by the formula (4) include compounds respectively represented by the following formulas (8) to (10).

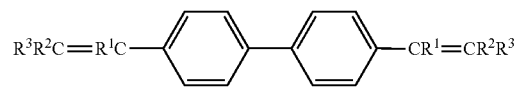

(8)

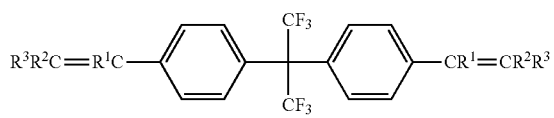

(9)

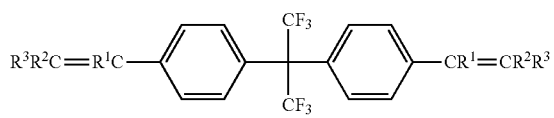

(10)

R$^1$, R$^2$, and R$^3$ in the formulas (8) to (10) are the same as defined above. t in the formula (10) is preferably 1 to 15, and more preferably 1 to 6.

Specific examples of the compound represented by the formula (3) include the following compounds (crosslinking agents (a) to (k)).

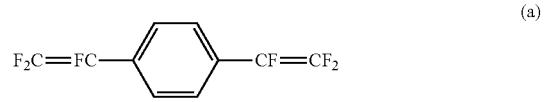

(a)

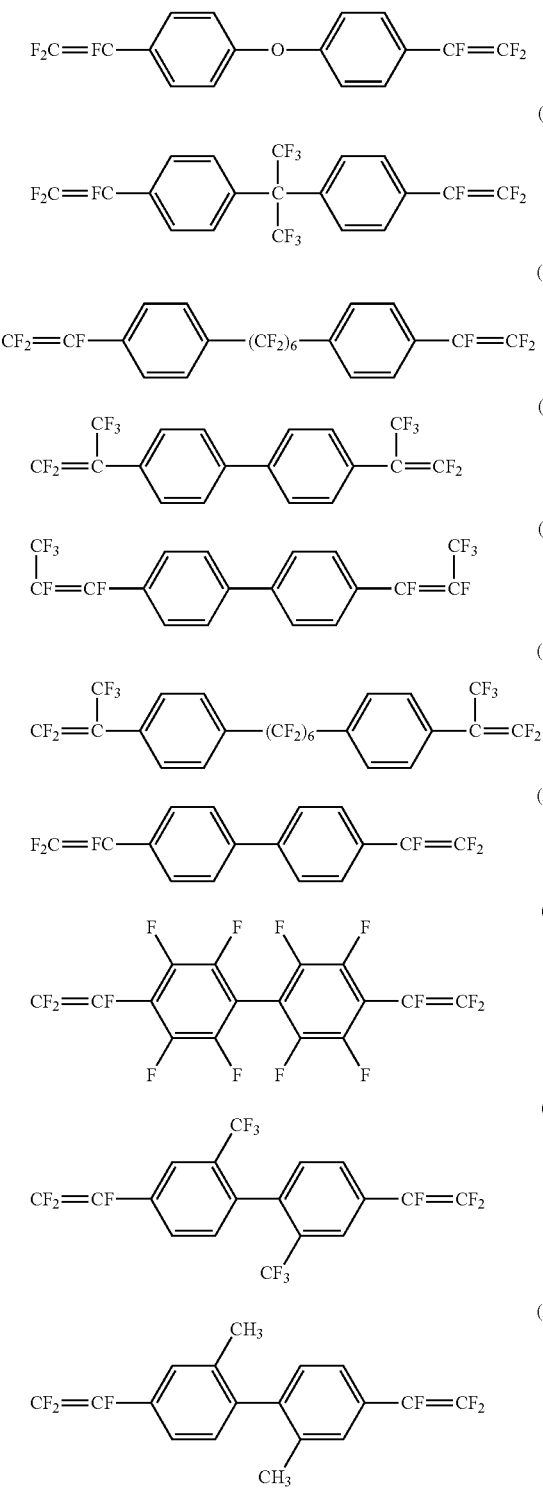

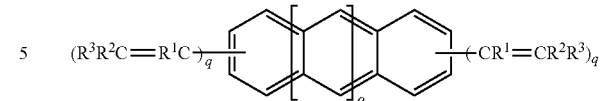

$R^1$, $R^2$, and $R^3$ in the formula (5) are the same as defined above.

o in the formula (5) is 1 or 0, and preferably 0.

q in the formula (5) are independently 1, 2, 3, or 4.

Specific examples of the compound represented by the formula (5) include a compound represented by the following formula (11) and a compound represented by the following formula (12).

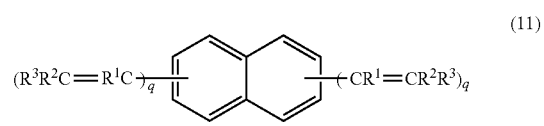

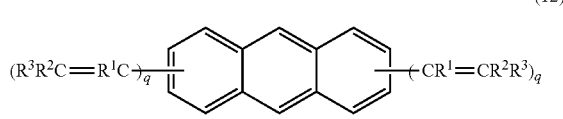

$R^1$, $R^2$, $R^3$, and q in the formulas (11) and (12) are the same as defined above.

When q in the formulas (11) and (12) are 1, it is possible to effect efficient crosslinking when the two groups represented by —$CR^1$=$CR^2R^3$ are situated farthest from each other.

Each hydrogen on the benzene ring(s) included in the formulas (1) to (12) is independently substituted or unsubstituted. Examples of the substituent include a fluorine atom, an alkyl group, a fluoroalkyl group, a cycloalkyl group, a fluorocycloalkyl group, a substituted or unsubstituted aryl group, and the like. The fluoroalkyl group and the fluorocycloalkyl group have a structure in which the alkyl group or the cycloalkyl group is fluorinated partially or completely. The alkyl group may be linear or branched. The number of carbon atoms of the alkyl group is preferably 1 to 15 (more preferably 1 to 6). The number of carbon atoms of the cycloalkyl group is preferably 3 to 8 (more preferably 3 to 6). The number of carbon atoms of the aryl group is preferably 6 to 18 (more preferably 6 to 12). Examples of a substituent that may substitute the aryl group include those mentioned above in connection with $R^1$.

Examples of the alkyl group include a methyl group, an ethyl group, a propyl group, and the like. Examples of the arylene group include a phenylene group, a naphthalenylene group, and the like.

A composition according to the invention includes the crosslinking agent (see above), a fluoroelastomer, and an initiator.

The crosslinking agent is preferably added in an amount of 0.5 to 30 mmol, more preferably 1 to 15 mmol, still more preferably 1.5 to 13 mmol, even more preferably 2 to 10 mmol, and yet more preferably 2.5 to 8 mmol, based on 100 g of the fluoroelastomer. There is a tendency that vapor resistance and heat resistance are improved as the amount of the crosslinking agent increases. Note that the composition may become hard if the amount of the crosslinking agent is too large.

Examples of the compound represented by the formula (1) or the compound that includes two or more structures represented by the formula (3) include a compound represented by the following formula (5).

The fluoroelastomer may be a perfluoroelastomer, or may be a partially fluorinated elastomer.

For example, the fluoroelastomer may include a repeating unit among repeating units respectively derived from the following monomers. The fluoroelastomer may include a repeating unit derived from one monomer, or may include repeating units respectively derived from two or more monomers.

$CF_2=CH_2$ (vinylidene fluoride)
$CF_2=CF_2$ (tetrafluoroethylene)
$CF_2=CFCF_3$ (hexafluoropropylene)
$CH_2=CH_2$
$CH_2=CHCH_3$ The fluoroelastomer used in connection with the invention preferably includes iodine and/or bromine (more preferably iodine) as a radical attack site during crosslinking (curing). A perfluoroelastomer that can be cured using a peroxidation method is disclosed in Patent Literature 1, for example.

A perfluoroelastomer normally includes iodine in a ratio of 0.001 to 5 wt %, and preferably 0.01 to 2.5 wt %, based on the total weight of the polymer. The iodine atoms may be present along the chain and/or at the terminal.

The perfluoroelastomer can be produced from a copolymer such as a perfluoroolefin that includes one ethylenically unsaturated bond (preferably at the terminal).

Examples of the comonomer include the following compounds.

$$CF_2=CFOR_{2f}((per)fluoroalkyl\ vinyl\ ether(PAVE))$$

wherein $R_{2f}$ is a (per)fluoroalkyl group having 1 to 6 carbon atoms, such as a trifluoromethyl group or a pentafluoropropyl group.

$$CF_2=CFOX_o((per)fluorooxyalkyl\ vinyl\ ether)$$

wherein $X_o$ is a (per)fluorooxyalkyl group having 1 to 12 carbon atoms that includes one or more ether groups, such as a perfluoro-2-propoxypropyl group.

$$CFX_2=CX_2OCF_2OR''_f \quad (I\text{-}B)$$

wherein $R''_f$ is a linear or branched (per)fluoroalkyl group having 2 to 6 carbon atoms, a cyclic (per)fluoroalkyl group having 5 or 6 carbon atoms, or a linear or branched (per) fluorooxyalkyl group having 2 to 6 carbon atoms and 1 to 3 oxygen atoms, and $X_2$ is F or H.

The (per)fluorovinyl ether represented by the formula (I-B) is preferably represented by the following formula.

$$CFX_2=CX_2OCF_2OCF_2CF_2Y \quad (II\text{-}B)$$

wherein Y is F or $OCF_3$, and $X_2$ is the same as defined above.

The perfluorovinyl ethers respectively represented by the following formulas are more preferable.

$$CF_2=CFOCF_2OCF_2CF_3 \quad (MOVE1)$$

$$CF_2=CFOCF_2OCF_2CF_2OCF_3 \quad (MOVE2)$$

Examples of a preferable monomer composition include the following compositions.
tetrafluoroethylene (TFE): 50 to 85 mol %, PAVE: 15 to 50 mol %
TFE: 50 to 85 mol %, MOVE: 15 to 50 mol %

The fluoroelastomer may also include a unit derived from vinylidene fluoride, a fluoroolefin having 3 to 8 carbon atoms that may include chlorine and/or bromine, and a non-flurorinated olefin having 3 to 8 carbon atoms.

A common initiator may be used as the initiator. Examples of the initiator include a peroxide, an azo compound, and the like.

The initiator is preferably added in an amount of 0.3 to 35 mmol, more preferably 1 to 15 mmol, and still more preferably 1.5 to 10 mmol, based on 100 g of the fluoroelastomer. There is a tendency that vapor resistance and heat resistance are improved as the amount of the initiator increases. Note that scorching or foaming may occur if the amount of the initiator is too large.

The fluoroelastomer composition may include a crosslinking assistant.

Examples of the crosslinking assistant include zinc oxide, activated alumina, magnesium oxide, a quaternary ammonium salt, a quaternary phosphonium salt, an amine, and the like. The crosslinking assistant improves the crosslinking efficiency and heat resistance. The crosslinking assistant is normally added in an amount of 0.1 to 10 g based on 100 g of the fluoroelastomer.

A filler may be added to the fluoroelastomer composition in order to improve mechanical strength. A material that is generally known as a filler for an elastomer may be used as the filler as long as the advantageous effects of the invention are not impaired. Examples of the filler include carbon black, silica, barium sulfate, titanium dioxide, a semicrystalline fluoropolymer, and a perfluoropolymer.

An appropriate amount of a thickener, a pigment, a coupling agent, an antioxidant, a stabilizer, or the like may optionally be added to the fluoroelastomer composition.

A crosslinked fluoroelastomer is obtained by crosslinking the composition according to the invention.

When using a 1-step heating process, the composition is preferably crosslinked by heating at 100 to 250° C. for 10 minutes to 5 hours.

When using a 2-step heating process, the raw material is normally put in a die, and crosslinked with pressing (primary crosslinking). For example, primary crosslinking is effected by heating at 150 to 200° C. for 5 to 60 minutes. The crosslinked product is then removed from the die, and subjected to secondary crosslinking. For example, secondary crosslinking is effected by heating at 150 to 300° C. for 1 to 100 hours. The crosslinking process may be performed using an electric furnace or the like. It is possible to suppress deformation and the like during use by a heat history through secondary crosslinking.

The crosslinking process may be performed in an inert gas atmosphere or air.

Nitrogen, helium, argon, or the like may be used as the inert gas. It is preferable to use nitrogen. The oxygen concentration in the inert gas atmosphere is preferably 10 ppm or less, and more preferably 5 ppm or less.

The crosslinked fluoroelastomer obtained using the production method according to the invention may be used as a seal material. The crosslinked fluoroelastomer may be formed in the shape of a gasket, a seal ring, or the like.

The production method according to the invention can produce a formed article that has a weight swelling change ratio of 70% or less before and after exposed to saturated water vapor at 300° C. for 22 hours (as measured using the method described in the examples). The weight swelling change ratio is preferably 65% or less, and more preferably 55% or less.

EXAMPLES

Synthesis of Fluorine-Containing Aromatic Compound

Example 1

Synthesis of Crosslinking Agent (a) ($CF_2$=CF-Ph-CF=$CF_2$)

A 500 ml two-necked flask equipped with a dry ice condenser and a septum in which the internal atmosphere had been replaced by Ar, was charged with a solution ($ZnCl_2$/THF solution) prepared by dissolving 2.18 g (16 mmol) of zinc chloride ($ZnCl_2$) in 30 ml of dehydrated tetrahydrofuran (THF). After cooling the $ZnCl_2$/THF solution to 15° C., 2 ml (24 mmol) of $CF_3CH_2F$ was added to the $ZnCl_2$/THF solution. After cooling the mixture to 10° C., 22 ml (33 mmol) of lithium diisopropylamide (ca. 20% in tetrahydrofuran/ethylbenzene/heptane, ca. 1.5 mol/L) was added to the mixture using a syringe (i.e., the needle was immersed in the $CF_3CH_2F$/$ZnCl_2$/THF solution, and lithium diisopropylamide was slowly added to the $CF_3CH_2F$/$ZnCl_2$/THF solution).

After stirring the mixture at 15° C. for 1 hour, 1.430 g (4.3 mmol) of 1,4-diiodobenzene and 175.3 mg (0.152 mmol) of tetrakis(triphenylphosphine)palladium(0) were added to the mixture, and the resulting mixture was stirred at room temperature for 24 hours. The mixture (solution) was concentrated to about 5 to 10 ml, and subjected to decantation using pentane, hexane, diethyl ether, and the like to extract the target compound. The extract was concentrated, and the concentrate was subjected to isolation by column chromatography (silica gel and hexane) to obtain the target compound ($CF_2$=CF-Ph-CF=$CF_2$) (wherein Ph is a p-phenylene group) as a transparent liquid (0.19 g, 0.8 mmol).

$^{19}F$ NMR ($CDCl_3$): −98.5 (dd, J=72.8, 34.0 Hz, 2F), −113.5 (dd, J=114.4, 70.4 Hz, 2F), −178.2 (dd, J=116.8, 36.4 Hz, 2F)

$^1H$ NMR ($CDCl_3$): 7.5 (s, 4H)

Example 2

Synthesis of Crosslinking Agent (h) ($CF_2$=CF-Ph-Ph-CF=$CF_2$)

A 500 ml two-necked flask equipped with a dry ice condenser and a septum in which the internal atmosphere had been replaced by Ar, was charged with a solution ($ZnCl_2$/THF solution) prepared by dissolving 6.814 g (50 mmol) of zinc chloride ($ZnCl_2$) in 100 ml of dehydrated tetrahydrofuran (THF). After cooling the $ZnCl_2$/THF solution to 15° C., 6 ml (72 mmol) of $CF_3CH_2F$ was added to the $ZnCl_2$/THF solution. After cooling the mixture to 10° C., 66.7 ml (100 mmol) of lithium diisopropylamide (ca. 20% in tetrahydrofuran/ethylbenzene/heptane, ca. 1.5 mol/L) was added to the mixture using a syringe (i.e., the needle was immersed in the $CF_3CH_2F$/$ZnCl_2$/THF solution, and lithium diisopropylamide was added to the $CF_3CH_2F$/$ZnCl_2$/THF solution so as to effect dissolution).

After stirring the mixture at 15° C. for 1 hour, 5.684 g (14 mmol) of 4,4'-diiodobiphenyl and 566.2 mg (0.49 mmol) of tetrakis(triphenylphosphine)palladium(0) were added to the mixture, and the resulting mixture was stirred at room temperature for 24 hours. The mixture (solution) was concentrated to about 20 ml, and subjected to decantation using pentane, hexane, diethyl ether, and the like to extract the target compound. After concentrating the extract, the concentrate was subjected to high-purity separation by column chromatography (silica gel and hexane), and recrystallization was effected using hexane and pentane to obtain the target compound ($CF_2$=CF-Ph-Ph-CF=$CF_2$) as a white solid (1.76 g, 5.6 mmol).

$^{19}F$ NMR ($CDCl_3$): −99.5 (dd, J=75.2, 33.6 Hz, 2F), −114.3 (dd, J=114.0, 72.8 Hz, 2F), −177.6 (dd, J=116.8, 34.0 Hz, 2F)

$^1H$ NMR ($CDCl_3$): 7.6 (d, J=8.4 Hz, 4H), 7.7 (d, J=8.8 Hz, 4H)

Example 3

Synthesis of Crosslinking Agent (c) ($CF_2$=CF-Ph-C($CF_3$)$_2$-Ph-CF=$CF_2$)

(1) Synthesis of I-Ph-C($CF_3$)$_2$-Ph-I

A 1,000 ml recovery flask was charged with 2.48 g (36 mmol) of sodium nitrite and 350 ml of distilled water, and the solution was cooled to 0° C. 15 ml of 6 M HCl was added to the solution at 1.5 ml/min. After the addition of a solution prepared by dissolving 5.01 g (15 mmol) of 2,2-bis(4-aminophenyl)hexafluoropropane in 30 ml of N,N-dimethylformamide at 2.5 to 3 ml/min, the mixture was stirred at 0 to 3° C. for 30 minutes. A solution prepared by dissolving 12.45 g (75 mmol) of potassium iodide in 30 ml of distilled water was slowly added dropwise to the mixture at 0 to 3° C., and N,N-dimethylformamide was added to the mixture (finally about 250 ml) every time precipitation occurred. The mixture was stirred at 0 to 3° C. for 1 hour, and stirred at room temperature for 12 hours.

The reaction solution was subjected to extraction with 500 ml of ether, washed several times with 100 ml of a sodium thiosulfate aqueous solution, and washed with distilled water, and N,N-dimethylformamide was removed. The mixture (solution) was concentrated to about 5 to 10 ml, and the concentrate was subjected to purification by column chromatography (silica gel and hexane) to obtain the target compound as white needle-like crystals (yield: 20%) (1.6 g, 3 mmol).

$^{19}F$ NMR ($CDCl_3$): −64.361 (s, 6F)
$^1H$ NMR ($CDCl_3$): 7.1 (d, J=8.4 Hz, 4H), 7.7 (d, J=8.8 Hz, 4H)

(2) Synthesis of $CF_2$=CF-Ph-C($CF_3$)$_2$-Ph-CF=$CF_2$

A 500 ml two-necked flask equipped with a dry ice condenser and a septum in which the internal atmosphere had been replaced by Ar, was charged with a solution ($ZnCl_2$/THF solution) prepared by dissolving 2.18 g (16 mmol) of zinc chloride ($ZnCl_2$) in 30 ml of dehydrated tetrahydrofuran (THF). After cooling the $ZnCl_2$/THF solution to 15° C., 2 ml (24 mmol) of $CF_3CH_2F$ was added to the $ZnCl_2$/THF solution. After cooling the mixture to 10° C., 22 ml (33 mmol) of lithium diisopropylamide (ca. 20% in tetrahydrofuran/ethylbenzene/heptane, ca. 1.5 mol/L) was added to the mixture using a syringe (i.e., the needle was immersed in the $CF_3CH_2F$/$ZnCl_2$/THF solution, and lithium diisopropylamide was slowly added to the $CF_3CH_2F$/$ZnCl_2$/THF solution).

After stirring the mixture at 15° C. for 1 hour, 2.391 g (4.3 mmol) of I-Ph-C($CF_3$)$_2$-Ph-I and 175.3 mg (0.152 mmol) of tetrakis(triphenylphosphine)palladium(0) were added to the mixture, and the resulting mixture was stirred at room temperature for 24 hours. The mixture (solution) was concentrated to about 5 to 10 ml, and subjected to decantation using pentane, hexane, diethyl ether, and the like to extract the target compound. The extract was concentrated, and the concentrate was subjected to isolation by column chromatography (silica gel and hexane) to obtain the target compound as a viscous transparent liquid (yield: 20%) (0.4 g, 0.86 mmol).

$^{19}$F NMR (CDCl$_3$): −64.2 (s, 6F), −98.1 (dd, J=70.4, 36.4 Hz, 2F), −113.2 (dd, J=116.8, 70.0 Hz, 2F), −178.8 (dd, J=114.4, 34.0 Hz, 2F)

$^1$H NMR (CDCl$_3$): 7.5 (dd, J=18, 8.8 Hz, 8H)

Example 4

Synthesis of Crosslinking Agent (d) (CF$_2$=CF-Ph-(CF$_2$)$_6$-Ph-CF=CF$_2$)

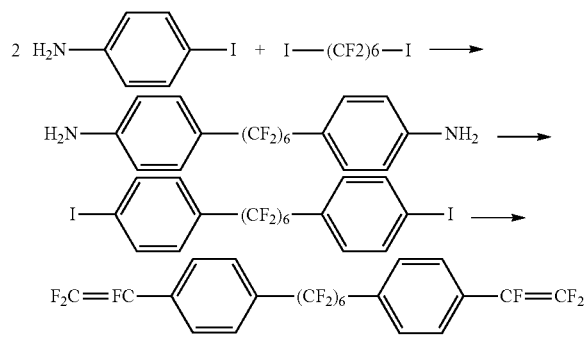

(1) Synthesis of NH$_2$-Ph-(CF$_2$)$_6$-Ph-NH$_2$ 2 mmol of 4-iodoaniline, 4 mmol of a Cu powder, and 1 mmol of dodecafluoro-1,6-diiodohexane were dissolved in dimethyl sulfoxide (DMSO), and the solution was heated at 160° C. for 3 hours in a nitrogen atmosphere under reflux. The reaction solution was subjected to extraction with ether, and washed with distilled water. The mixture (solution) was concentrated to about 5 to 10 ml, and the concentrate was subjected to purification by column chromatography (silica gel and hexane).

(2) Synthesis of I-Ph-(CF$_2$)$_6$-Ph-I

A 1,000 ml recovery flask was charged with 36 mmol of sodium nitrite and 350 ml of distilled water, and the solution was cooled to 0° C. 15 ml of 6 M HCl was added to the solution at 1.5 ml/min. After the addition of a solution prepared by dissolving 15 mmol of NH$_2$-Ph-(CF$_2$)$_6$-Ph-NH$_2$ in 30 ml of N,N-dimethylformamide at 2.5 to 3 ml/min, the mixture was stirred at 0 to 3° C. for 30 minutes. A solution prepared by dissolving 75 mmol of potassium iodide in 30 ml of distilled water was slowly added dropwise to the mixture at 0 to 3° C., and N,N-dimethylformamide was added to the mixture (finally about 250 ml) every time precipitation occurred. The mixture was stirred at 0 to 3° C. for 1 hour, and stirred at room temperature for 12 hours.

The reaction solution was subjected to extraction with 500 ml of ether, washed several times with 100 ml of a sodium thiosulfate aqueous solution, and washed with distilled water, and N,N-dimethylformamide was removed. The mixture (solution) was concentrated to about 5 to 10 ml, and the concentrate was subjected to purification by column chromatography (silica gel and hexane).

(3) Synthesis of CF$_2$=CF-Ph-(CF$_2$)$_6$-Ph-CF=CF$_2$

A 500 ml two-necked flask equipped with a dry ice condenser and a septum in which the internal atmosphere had been replaced by Ar, was charged with a solution (ZnCl$_2$/THF solution) prepared by dissolving 16 mmol of zinc chloride (ZnCl$_2$) in 30 ml of dehydrated tetrahydrofuran (THF). After cooling the ZnCl$_2$/THF solution to 15° C., 24 mmol of CF$_3$CH$_2$F was added to the ZnCl$_2$/THF solution. After cooling the mixture to 10° C., 33 mmol of lithium diisopropylamide (ca. 20% in tetrahydrofuran/ethylbenzene/heptane, ca. 1.5 mol/L) was added to the mixture using a syringe (i.e., the needle was immersed in the CF$_3$CH$_2$F/ZnCl$_2$/THF solution, and lithium diisopropylamide was slowly added to the CF$_3$CH$_2$F/ZnCl$_2$/THF solution).

After stirring the mixture at 15° C. for 1 hour, 4.3 mmol of I-Ph-(CF$_2$)$_6$-Ph-I and 0.152 mmol of tetrakis(triphenylphosphine)palladium(0) were added to the mixture, and the resulting mixture was stirred at room temperature for 24 hours. The mixture (solution) was concentrated to about 5 to 10 ml, and subjected to decantation using pentane, hexane, diethyl ether, and the like to extract the target compound. The extract was concentrated, and the concentrate was subjected to isolation by column chromatography (silica gel and hexane).

Melting point: 93° C.

Example 5

Synthesis of Crosslinking Agent (f) (CFCF$_3$=CF-Ph-Ph-CF=CFCF$_3$)

A 500 ml two-necked flask equipped with a septum in which the internal atmosphere had been replaced by Ar, was charged with 12.18 g (30 mmol) of 4,4'-diiodobiphenyl and 350 ml of dehydrated tetrahydrofuran (THF), and the mixture was stirred at −80° C. 42 ml (70 mmol) of n-butyllithium (hexane solution (concentration: about 15%), about 1.6 mol/L) was slowly added dropwise to the resulting suspension, and the mixture was stirred at −50° C. for 30 minutes to prepare Li-Ph-Ph-Li.

A 500 ml two-necked flask equipped with a dry ice condenser and a septum in which the internal atmosphere had been replaced by Ar, was charged with 300 ml of THF. After cooling the THF to −80° C., 11 ml (90 mmol) of 1,1,1,2,3,3-hexafluoropropylene was added with bubbling. After the addition of Li-Ph-Ph-Li (prepared as described above) using a syringe (i.e., the needle was immersed in the hexafluoropropylene/THF solution, and Li-Ph-Ph-Li was added to the hexafluoropropylene/THF solution so as to effect dissolution), the mixture was stirred at −80° C. for 1 hour. The mixture was then slowly heated to room temperature over 2 hours, and stirred overnight.

The mixture (solution) that had been stirred overnight was concentrated to about 20 ml, and subjected to decantation using hexane to extract the target compound. After concentrating the extract, the concentrate was subjected to high-purity separation by column chromatography (silica gel and n-hexane). The resulting crystals were dissolved in hexane, and subjected to concentration and recrystallization (washed several times with pentane) to obtain the target compound (CFCF$_3$=CF-Ph-Ph-CF=CFCF$_3$) as white crystals (yield: 30%) (4 g, 12 mmol).

$^{19}$F NMR (CDCl$_3$): −67.3 (dd, J=23.2, 10.4 Hz, 6F), −147.2 (q, J=46.8, 23.2 Hz, 1F), −147.2 (q, J=46.8, 23.6 Hz, 1F), −168.7 (q, J=23.2, 12.8 Hz, 1F), −169.0 (q, J=23.6, 10.4 Hz, 1F)

$^1$H NMR (CDCl$_3$): 7.78 (dd, J=26, 8.4 Hz, 8H)

Melting point: 138° C.

Production of Formed Article of Crosslinked Fluoroelastomer

Example 6

PFR94 (manufactured by Solvay) (fluoroelastomer), PERHEXA 25B-40 (manufactured by NOF Corporation) (2,5-dimethyl-2,5-di(t-butylperoxy)hexane) (initiator) (4 g (5.5 mmol) based on 100 g of the fluoroelastomer), ZnO (manufactured by Sakai Chemical Industry Co., Ltd.) (crosslinking assistant) (3 g based on 100 g of the fluoroelastomer), Activated Alumina KC-501 (manufactured by Sumitomo Chemical Co., Ltd.) (crosslinking assistant) (3 g based on 100 g of the fluoroelastomer), and the crosslinking agent (a) produced in Example 1 (4.2 mmol based on 100 g of the fluoroelastomer) were kneaded using an open roll, placed in a die, and heated at 170° C. for 15 minutes to effect pressing and primary crosslinking. The mixture was removed from the die, and heated at 290° C. for 16 hours in air (after being heated over 8 hours) to obtain a formed article of a crosslinked fluoroelastomer. The formed article had a disc-like shape (diameter: 40 mm, thickness: 2 mm) or an O-ring shape (ring width: 3.53 mm, inner diameter: 24.99 mm).

Example 7

PFR94 (manufactured by Solvay) (fluoroelastomer), PERHEXA 25B (manufactured by NOF Corporation) (initiator) (1 g (3.4 mmol) based on 100 g of the fluoroelastomer), and the crosslinking agent (h) produced in Example 2 (11.1 mmol based on 100 g of the fluoroelastomer) were kneaded using an open roll. The mixture was treated in the same manner as in Example 6 to obtain a formed article.

Comparative Example 1

A crosslinked fluoroelastomer was produced, and a formed article was obtained in the same manner as in Example 6, except that a fluorinated diene (1,6-divinylperfluorohexane) (CH$_2$=CH—(CF$_2$)$_6$—CH=CH$_2$) (manufactured by TOSOH F-TECH, INC.) (4.2 mmol based on 100 g of the fluoroelastomer) was used instead of the crosslinking agent (a).

Comparative Example 2

A crosslinked fluoroelastomer was produced, and a formed article was obtained in the same manner as in Example 7, except that a fluorinated diene (1,6-divinylperfluorohexane) (CH$_2$=CH—(CF$_2$)$_6$—CH=CH$_2$) (manufactured by TOSOH F-TECH, INC.) (4.2 mmol based on 100 g of the fluoroelastomer) was used instead of the crosslinking agent (h).

Comparative Example 3

A crosslinked fluoroelastomer was produced, and a formed article was obtained in the same manner as in Example 6, except that TAIC (manufactured by Nippon Kasei Chemical Co., Ltd.) (4.2 mmol based on 100 g of the fluoroelastomer) was used instead of the crosslinking agent (a).

Evaluation Example 1

A disc having a diameter of 13 mm was stamped out from each of the disc-like formed articles obtained in Example 6 and Comparative Examples 1 and 3, and subjected to a heat resistance test (dry heat 320° C.) as described below. The results are shown in Table 1.

The disc was heated for 70 hours or 92 hours in a Geer oven (320° C.), and the weight change ratio (weight reduction ratio) due to heating was calculated and evaluated. A change in external appearance was also observed and evaluated. The weight change ratio (weight reduction ratio) was calculated using the following expression.

Weight reduction ratio (%)=((weight before heating)−(weight after heating))/(weight before heating)×100

A case where a change in external appearance was not observed is indicated as "No change", a case where melting was observed, but a change in shape was not observed is indicated as "Some melting", a case where melting was observed, and chipping was observed is indicated as "Melting 1", a case where melting was observed, and an inner hollow part was formed is indicated as "Melting 2", and a case where melting was observed, and the shape was not maintained is indicated as "Melting 3".

TABLE 1

|  | After 320° C. 70 hr | | After 320° C. 92 hr | |
| --- | --- | --- | --- | --- |
|  | Weight reduction ratio (%) | External appearance | Weight reduction ratio (%) | External appearance |
| Example 6 | 2.5 | No change | 2.9 | No change |
| Comparative Example 1 | 4.0 | No change | 4.6 | No change |
| Comparative Example 3 | 3.7 | Melting 1 | 4.2 | Melting 3 |

Evaluation Example 2

A disc having a diameter of 13 mm was stamped out from each of the disc-like formed articles obtained in Examples 6 and 7 and Comparative Examples 1 and 2, and subjected to the heat resistance test in the same manner as in Evaluation Example 1, except that the test was performed at 330° C. for 22 hours or 44 hours. The results are shown in Table 2. Note that the symbol "-" in Table 2 means that the formed article sample was not subjected to the 44-hour test since the formed article sample was melted (i.e., the shape was not maintained) when subjected to the 22-hour test.

TABLE 2

|  | After 330° C. 22 hr | | After 330° C. 44 hr | |
| --- | --- | --- | --- | --- |
|  | Weight reduction ratio (%) | External appearance | Weight reduction ratio (%) | External appearance |
| Example 6 | 2.2 | No change | 3.1 | No change |
| Example 7 | 2.2 | No change | 3.3 | No change |
| Comparative Example 1 | 4.0 | No change | 5.1 | Melting 2 |

TABLE 2-continued

|  | After 330° C. 22 hr | | After 330° C. 44 hr | |
| --- | --- | --- | --- | --- |
|  | Weight reduction ratio (%) | External appearance | Weight reduction ratio (%) | External appearance |
| Comparative Example 2 | 11.2 | Melting 3 | — | — |

Evaluation Example 3

A disc having a diameter of 13 mm was stamped out from each of the disc-like formed articles obtained in Examples 6 and 7 and Comparative Examples 1 and 2, and the vapor resistance of the resulting disc was evaluated as described below. The results are shown in Table 3.

(1) Measurement of Weight Swelling Ratio

The weight swelling ratio of the formed article before being subjected to the vapor resistance test (300° C.) was measured.

The formed article was immersed in a perfluorocarbon solution ("Fluorinert FC-3283" manufactured by 3M Japan Limited) at room temperature (21 to 25° C.) for 72 hours, and the weight swelling ratio due to immersion was calculated using the following expression.

Weight swelling ratio (%)=((weight after immersion)−(weight before immersion))/(weight before immersion)×100

(2) Vapor Resistance Test (300° C.)

The formed article was then subjected to the vapor resistance test (300° C.).

Specifically, the formed article was exposed to saturated water vapor at 300° C. for 22 hours.

(3) Measurement of Weight Swelling Ratio after Vapor Resistance Test (300° C.)

The formed article subjected to the vapor resistance test (300° C.) was immersed in a perfluorocarbon solution at room temperature (21 to 25° C.) for 72 hours, and the weight swelling ratio after the vapor resistance test (300° C.) was calculated in the same manner as in (1).

The change ratio (%) with respect to the weight swelling ratio due to the vapor resistance test (300° C.) was calculated using the "weight swelling ratio before the vapor resistance test" and the "weight swelling ratio after the vapor resistance test" (see the following expression).

Change ratio (%)=((weight swelling ratio after vapor resistance test)−(weight swelling ratio before vapor resistance test))/(weight swelling ratio before vapor resistance test)×100

The external appearance of the formed article that was subjected to the vapor resistance test (300° C.) and then immersed in the perfluorocarbon solution was observed. The results are shown in Table 3. Note that the symbol "-" in Table 3 means that the weight swelling ratio could not be measured since the formed article sample was melted.

TABLE 3

| | Weight swelling ratio (%) | | | |
| --- | --- | --- | --- | --- |
|  | Before vapor resistance test | After vapor resistance test | Change ratio (%) | External appearance |
| Example 6 | 159 | 257 | 62 | No change |
| Example 7 | 174 | 250 | 44 | No change |

TABLE 3-continued

| | Weight swelling ratio (%) | | | |
| --- | --- | --- | --- | --- |
|  | Before vapor resistance test | After vapor resistance test | Change ratio (%) | External appearance |
| Comparative Example 1 | 146 | 336 | 130 | No change |
| Comparative Example 3 | 92 | — | — | Foaming, swelling, and melting were observed |

Examples 8 to 11

A formed article was obtained in the same manner as in Example 6, except that the components shown in Table 4 were used in the amounts shown in Table 4, and kneaded using an open roll. In Example 8, an O-ring (ring width: 3.53 mm, inner diameter: 24.99 mm) was obtained as the formed article. In Examples 9 to 11, a disc (diameter: 5 mm, thickness: 1 mm) and a strip (length: 20 mm, width: 10 mm, thickness: 1 mm) were obtained as the formed article.

PERBUTYL P in Table 4 is α,α'-di(t-butylperoxy)diisopropylbenzene (manufactured by NOF Corporation), and PERCUMYL D in Table 4 is dicumyl peroxide (manufactured by NOF Corporation).

In Table 4, each value listed in connection with the initiator refers to the amount (mmol) based on 100 g of the fluoroelastomer, and each value listed in connection with the crosslinking agent refers to the amount (mmol) based on 100 g of the fluoroelastomer.

TABLE 4

|  |  | Example 8 | Example 9 | Example 10 | (mmol) Example 11 |
| --- | --- | --- | --- | --- | --- |
| Polymer | PFR94 | 100 | 100 | 100 | 100 |
| Initiator | PERHEXA 25B | 5.2 | 5.2 |  |  |
|  | PERBUTYL P |  |  | 2.7 |  |
|  | PERCUMYL D |  |  |  | 4.1 |
| Crosslinking agent | Crosslinking agent (c) | 6.5 |  |  |  |
|  | Crosslinking agent (d) |  | 6.3 |  |  |
|  | Crosslinking agent (e) |  |  | 7.2 |  |
|  | Crosslinking agent (f) |  |  |  | 5.7 |

Evaluation Example 4

An arc-shaped sample (length: 10 mm) obtained by cutting the O-ring obtained in Example 8, and the discs obtained in Examples 9 to 11 were subjected to the heat resistance test in the same manner as in Evaluation Example 2. The results are shown in Table 5.

TABLE 5

|  | After 330° C. 22 hr | | After 330° C. 44 hr | |
| --- | --- | --- | --- | --- |
|  | Weight reduction ratio (%) | External appearance | Weight reduction ratio (%) | External appearance |
| Example 8 | 2.0 | No change | 3.4 | No change |
| Example 9 | 2.0 | No change | 3.5 | No change |
| Example 10 | 2.3 | No change | 4.5 | No change |
| Example 11 | 2.3 | No change | 4.7 | No change |

Evaluation Example 5

The vapor resistance of the O-ring obtained in Example 8 and the strips obtained in Examples 9 to 11 was evaluated in the same manner as in Evaluation Example 3. The results are shown in Table 6.

TABLE 6

|  | Weight swelling ratio (%) | | | |
| --- | --- | --- | --- | --- |
|  | Before vapor resistance test | After vapor resistance test | Change ratio (%) | External appearance |
| Example 8 | 280 | 343 | 23 | No change |
| Example 9 | 413 | 581 | 41 | No change |
| Example 10 | 599 | 772 | 29 | No change |
| Example 11 | 545 | 721 | 32 | No change |

INDUSTRIAL APPLICABILITY

The fluorine-containing aromatic compound or the crosslinking agent according to the invention can be used as a crosslinking agent for a fluoroelastomer. The crosslinked fluoroelastomer according to the invention can be used as a seal material for which heat resistance and vapor resistance are required.

Although only some exemplary embodiments and/or examples of the invention have been described in detail above, those skilled in the art will readily appreciate that many modifications are possible in the exemplary embodiments and/or examples without materially departing from the novel teachings and advantages of the invention. Accordingly, all such modifications are intended to be included within the scope of the invention.

The documents described in the specification, and the specification of the Japanese patent application to which the present application claims priority under the Paris Convention, are incorporated herein by reference in their entirety.

The invention claimed is:

1. A crosslinking agent comprising:
a compound represented by a formula (1),

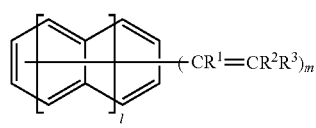

(1)

wherein $R^1$ is a fluorine atom, an alkyl group having 1 to 6 carbon atoms, $R^2$, and $R^3$ are independently a fluroine atom, an alkyl group, or a fluoroalkyl group, wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, a fluoroalkyl group, wherein m is an integer of from 2 to 6, l is an integer of from 0 to 2, and wherein each hydrogen on the benzene ring(s) is optionally substituted with a substituent.

2. The crosslinking agent according to claim 1, wherein the compound represented by the formula (1) is a compound represented by a formula (2),

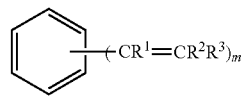

(2)

wherein $R^1$, $R^2$, $R^3$, and m are the same as defined for the formula (1), and each hydrogen on the benzene ring is optionally substituted with a substituent.

3. A crosslinking agent comprising:
a compound represented by a formula (4),

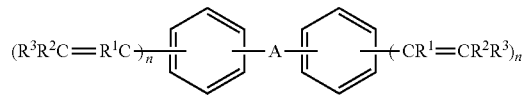

(4)

wherein A is a single bond, —O—, —S—, a linear or a branched alkylene group, a cycloalkylene group, or an arylene group that is optionally fluorinated either partially or completely, wherein $R^1$, $R^2$, and $R^3$, are independently a fluorine atom, an alkyl group, or a fluoroalkyl group, p1 wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, or a fluoroalkyl group, and wherein n are independently an integer of from 1 to 5.

4. A crosslinking agent comprising:
a compound represented by a formula (5),

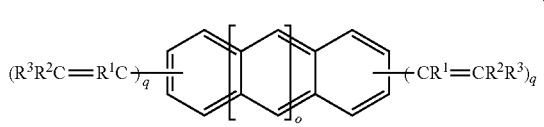

(5)

wherein $R^1$, $R^2$, and $R^3$ are independently a fluorine atom, an alkyl group, or a fluoroalkyl group, wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, or a fluoroalkyl group, wherein o is 1 or 0, q are independently an integer of from 1 to 3, and wherein each hydrogen on the benzene rings is optionally substituted with a sub stituent.

5. A composition comprising a fluoroelastomer, an initiator, and a crosslinking agent:
the crosslinking agent comprising a compound represented by a formula (1),

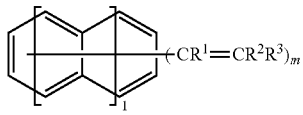

(1)

wherein $R^1$, $R^2$, and $R^3$ are independently a fluorine atom, an alkyl group, a fluoroalkyl group, or a substituted or unsubstituted aryl group, wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, a fluoroalkyl group, a substituted aryl group or unsubstituted aryl group, wherein m is an integer of from 2 to 6, l is an integer of from 0 to 2, and wherein each hydrogen on the benzene ring(s) is optionally substituted with a sub stituent.

6. The composition according to claim 5, comprising the crosslinking agent in an amount of 0.5 to 30 mmol based on 100 g of the fluoroelastomer.

7. The composition according to claim 5, comprising the initiator in an amount of 0.3 to 35 mmol based on 100 g of the fluoroelastomer.

8. A crosslinked fluoroelastomer obtained by crosslinking the composition according to claim 5.

9. A formed article comprising the crosslinked fluoroelastomer according to claim 8.

10. The formed article according to claim 9, the formed article being a seal material.

11. A compound represented by a formula (1),

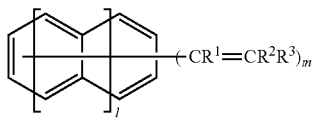

(1)

wherein $R^1$, $R^2$, and $R^3$ are independently a fluorine atom, an alkyl group, a fluoroalkyl group, or a substituted or unsubstituted aryl group, wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, a fluoroalkyl group, a substituted aryl group or unsubstituted aryl group, wherein m is an integer of from 2 to 6, l is an integer of from 0 to 2, and wherein each hydrogen on the benzene ring(s) is optionally substituted with a substituent.

12. The compound according to claim 11, the compound being a compound represented by a formula (2),

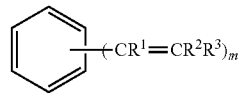

(2)

wherein $R^1$, $R^2$, $R^3$, and m are the same as defined for the formula (1), and each hydrogen on the benzene ring is optionally substituted with a substituent.

13. A compound represented by a formula (4),

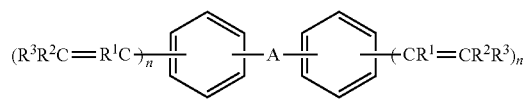

(4)

wherein A is a single bond, —O—, —S—, a linear or a branched alkylene group, a cycloalkylene group, or an arylene group that is optionally fluorinated either partially or completely, wherein $R^1$, $R^2$, and $R^3$ are independently a fluorine atom, an alkyl group, or a fluoroalkyl group, and wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, a fluoroalkyl group, n are independently an integer of from 1 to 5.

14. A compound represented by a formula (5),

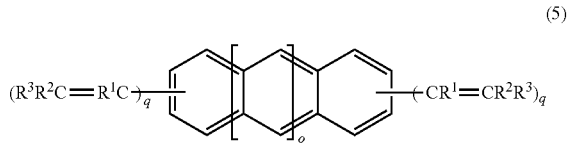

(5)

wherein $R^1$, $R^2$, and $R^3$ are independently a fluorine atom, an alkyl group, or a fluoroalkyl group, wherein a plurality of $R^1$ are identical or different, a plurality of $R^2$ are identical or different, and a plurality of $R^3$ are identical or different, provided that at least one of $R^1$, $R^2$, and $R^3$ is a fluorine atom or a fluorine atom-containing group and at least one of $R^1$, $R^2$, and $R^3$ is an alkyl group, a fluoroalkyl group, wherein o is 1 or 0, q are independently an integer of from 1 to 3, and wherein each hydrogen on the benzene rings is optionally substituted with a substituent.

15. A corsslinking agent comprising:
a compound represented by a formula (4),

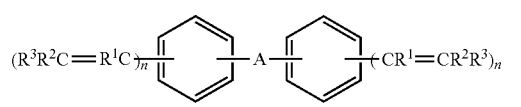

(4)

wherein A is a single bond, —O—, —S—, a linear or a branched alkylene group, a cycloalkylene group, or an arylene group that is optionally fluorinated either partially or completely, wherein $R^1$, $R^2$, and $R^3$, are independently a fluorine atom, an alkyl group, a fluoroalkyl group, or a substituted or unsubstituted aryl group, wherein a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, and wherein n are independently an integer of from 1 to 5, provided that a compound in which A is a single bond, $R^1$, $R^2$, and $R^3$ are a fluorine atom, and two n are 1 is excluded.

16. The crosslinking agent according to claim 15, wherein, in the formula (4), A is a single bond, -O-, -S-, a linear or a branched alkylene group having 6 to 15 carbon atoms, a cycloalkylene group, or an arylene group; and wherein the heteroatom-containing group, the linear or branched alkylene group, the cycloalkylene group, and the arylene group may be fluorinated partially or completely.

17. A compound represented by a formula (4),

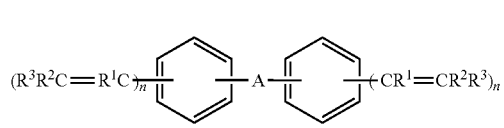

(4)

wherein A is a single bond, —O—, —S—, a linear or a branched alkylene group, a cycloalkylene group, or an arylene group that is optionally fluorinated either partially or completely, wherein $R^1$, $R^2$, and $R^3$ are independently a fluorine atom, an alkyl group, a fluoroalkyl group, or a substituted or unsubstituted aryl group, wherein a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, and wherein n are independently an integer of from 1 to 5, provided that a compound in which A is a single bond, $R^1$, $R^2$, and $R^3$ are a fluorine atom, and two n are 1 is excluded.

18. The compound according to claim 17, wherein, in the formula (4), A is a single bond, —O—, —S—, a linear or a branched alkylene group having 6 to 15 carbon atoms, a cycloalkylene group, or an arylene group; and wherein heteroatom-containing group, the linear or branched alkylene group, the cycloalkylene group, and the arylene group may be fluorinated partially or completely.

19. A compound represented by a formula (4),

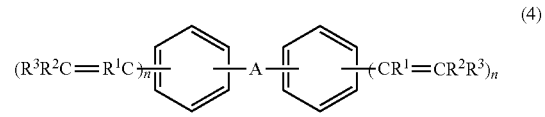

(4)

wherein A is a single bond, —O—, —S—, a linear alkylene group, a cycloalkylene group, or an arylene group that is optionally fluorinated either partially or completely, wherein $R^1$, $R^2$, and $R^3$ are independently a fluorine atom, an alkyl group, a fluoroalkyl group, or a substituted or unsubstituted aryl group, wherein a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, wherein n are independently an integer of from 1 to 5, provided that a compound in which A is a single bond, $R^1$, $R^2$, and $R^3$ are a fluorine atom, and two n are 1 is excluded, and wherein each hydrogen on the benzene rings is optionally substituted with a substituent.

20. A composition comprising a fluoroelastomer, an initiator, and a crosslinking agent:

the crosslinking agent comprising a compound represented by a formula (4),

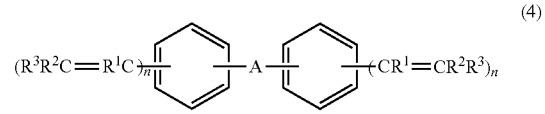

(4)

wherein A is a single bond, —O—, —S—, a heteroatom-containing group, a linear or a branched alkylene group, a cycloalkylene group, or an arylene group that is optionally fluorinated either partially or completely, wherein $R^1$, $R^2$, and $R^3$ are independently a fluorine atom, an alkyl group, a fluoroalkyl group, or a substituted or unsubstituted aryl group, wherein a plurality of $R^1$ are identical or different, a plurality of $R^2$ are identical or different, a plurality of $R^3$ are identical or different, provided that at least one of $R^1$, $R^2$, and $R^3$ is a fluorine atom or a fluorine atom-containing group, wherein n are independently an integer of from 1 to 5, provided that a compound in which A is a single bond, $R^1$, $R^2$, and $R^3$ are a fluorine atom, and two n are 1 is excluded, and wherein each hydrogen on the benzene rings is optionally substituted with a substituent.

* * * * *